(12) United States Patent
Fritz et al.

(10) Patent No.: US 9,901,296 B2
(45) Date of Patent: Feb. 27, 2018

(54) BLOOD LANCET WITH HYGIENIC TIP PROTECTION

(75) Inventors: Michael Fritz, Buerstadt (DE);
Herbert Argauer, Pirk (DE); Hans List, Hesseneck-Kailbach (DE);
Thomas Weiss, Mannheim (DE);
Frank Deck, Niederkirchen (DE);
Claudio Immekus, Tutschfelden (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1852 days.

(21) Appl. No.: 12/253,702

(22) Filed: Oct. 17, 2008

(65) Prior Publication Data

US 2009/0043325 A1  Feb. 12, 2009

Related U.S. Application Data

(63) Continuation of application No. 10/204,568, filed as application No. PCT/EP01/02198 on Feb. 28, 2001, now abandoned.

(30) Foreign Application Priority Data

Mar. 4, 2000  (DE) ................................. 100 10 694

(51) Int. Cl.
*A61B 5/00* (2006.01)
*A61B 5/151* (2006.01)
*A61B 5/15* (2006.01)

(52) U.S. Cl.
CPC .... *A61B 5/15165* (2013.01); *A61B 5/150022* (2013.01); *A61B 5/15142* (2013.01);
(Continued)

(58) Field of Classification Search
CPC ............ A61B 5/15142; A61B 5/15146; A61B 5/150022; A61B 5/150259; A61B 5/150412; A61B 5/150572
(Continued)

(56) References Cited

U.S. PATENT DOCUMENTS 2,714,890 A   8/1955   Vang
3,030,959 A   4/1962   Gruner
(Continued)

FOREIGN PATENT DOCUMENTS

CH        289191       11/1953
DE      1 079 275       4/1960
(Continued)

OTHER PUBLICATIONS

DE 1 079 275 English language translation.
(Continued)

*Primary Examiner* — Vy Bui
(74) *Attorney, Agent, or Firm* — Woodard, Emhardt, Moriarty, McNett & Henry LLP

(57) ABSTRACT

The invention concerns lancets with a lancet needle, the tip of the lancet needle being embedded in an elastic material. Furthermore the invention concerns lancets where the tip of the lancet needle is surrounded by a hollow body which partially consists of an elastic material that can be pierced by the tip of the lancet needle during the lancing process and which reseals the tip of the lancet needle in the hollow body when it is retracted. In addition the invention concerns a lancet magazine in which the lancets are accommodated in individual chambers, each chamber having an opening through which the tip of the lancet needle can pass, which is sealed by an elastic material. Finally the invention concerns the use of an elastic material as a component of a lancet or a lancet magazine to maintain the sterility of at
(Continued)

least the tip of a lancet needle in the unused state and to hygienically protect at least the tip of a lancet needle in the used state.

16 Claims, 3 Drawing Sheets

(52) U.S. Cl.
CPC ...... *A61B 5/15151* (2013.01); *A61B 5/15171* (2013.01); *A61B 5/15176* (2013.01); *A61B 5/15186* (2013.01); *A61B 5/150412* (2013.01); *A61B 5/150503* (2013.01); *A61B 5/150572* (2013.01); *A61B 5/150633* (2013.01)

(58) Field of Classification Search
USPC .................................................. 606/141, 181
See application file for complete search history.

(56) References Cited

U.S. PATENT DOCUMENTS

| | | | |
|---|---|---|---|
| 3,208,452 A | 9/1965 | Stern | |
| 3,086,288 A | 4/1969 | Balamuth et al. | |
| 3,673,475 A | 6/1972 | Britton, Jr. | |
| 3,832,776 A | 9/1974 | Sawyer | |
| 4,077,406 A | 3/1978 | Sandhage et al. | |
| 4,154,228 A | 5/1979 | Feldstein et al. | |
| 4,203,446 A | 5/1980 | Hofert et al. | |
| 4,223,674 A | 9/1980 | Fluent et al. | |
| 4,230,118 A | 10/1980 | Holman et al. | |
| 4,356,826 A | 11/1982 | Kubota | |
| 4,398,544 A | 8/1983 | Nugent et al. | |
| 4,442,836 A | 4/1984 | Meinecke et al. | |
| 4,449,529 A | 5/1984 | Burns et al. | |
| 4,462,405 A | 7/1984 | Erhlich | |
| 4,518,384 A | 5/1985 | Tarello et al. | |
| 4,535,773 A | 8/1985 | Yoon | |
| 4,548,201 A * | 10/1985 | Yoon | 606/141 |
| 4,553,541 A | 11/1985 | Burns et al. | |
| 4,627,445 A | 12/1986 | Garcia et al. | |
| 4,635,633 A | 1/1987 | Hufnagle | |
| 4,637,403 A | 1/1987 | Garcia et al. | |
| 4,653,513 A | 3/1987 | Dombrowski | |
| 4,660,570 A | 4/1987 | Dombrowski | |
| 4,695,274 A | 9/1987 | Fox | |
| 4,750,489 A | 6/1988 | Berkman et al. | |
| 4,787,398 A | 11/1988 | Garcia et al. | |
| 4,794,926 A | 1/1989 | Munsch et al. | |
| 4,823,806 A | 4/1989 | Bajada | |
| 4,883,068 A | 11/1989 | Dechow | |
| 4,889,117 A | 12/1989 | Stevens | |
| 4,924,879 A | 5/1990 | O'Brien | |
| 4,983,178 A | 1/1991 | Schnell | |
| 4,995,402 A | 2/1991 | Smith et al. | |
| 5,029,583 A | 7/1991 | Meserol et al. | |
| 5,035,704 A | 7/1991 | Lambert et al. | |
| 5,047,044 A | 9/1991 | Smith et al. | |
| 5,097,810 A | 3/1992 | Fishman et al. | |
| 5,122,123 A | 6/1992 | Vaillancourt | |
| 5,145,565 A | 9/1992 | Kater et al. | |
| 5,152,775 A | 10/1992 | Ruppert | |
| 5,222,504 A | 1/1993 | Solomon | |
| 5,188,118 A | 2/1993 | Terwilliger | |
| 5,189,751 A | 3/1993 | Giuliani et al. | |
| 5,201,324 A | 4/1993 | Swierczek | |
| 5,207,699 A | 5/1993 | Coe | |
| 5,231,993 A | 8/1993 | Haber et al. | |
| 5,279,294 A | 1/1994 | Anderson et al. | |
| 5,304,192 A | 4/1994 | Crouse | |
| 5,312,366 A | 5/1994 | Vaillancourt | |
| 5,313,969 A | 5/1994 | Hsieh | |
| 5,318,583 A | 6/1994 | Rabenau et al. | |
| 5,318,584 A | 6/1994 | Lange et al. | |
| 5,320,808 A | 6/1994 | Holen et al. | |
| 5,360,012 A | 11/1994 | Ebara et al. | |
| 5,360,410 A | 11/1994 | Wacks | |
| 5,368,047 A | 11/1994 | Suzuki et al. | |
| 5,385,571 A | 1/1995 | Morita | |
| 5,395,387 A | 3/1995 | Burns | |
| 5,415,169 A | 5/1995 | Siczek et al. | |
| 5,423,847 A | 6/1995 | Strong et al. | |
| 5,472,427 A | 12/1995 | Rammler | |
| 5,474,084 A | 12/1995 | Cunniff | |
| RE35,203 E | 4/1996 | Wakalopulos | |
| 5,514,152 A | 5/1996 | Smith | |
| 5,529,074 A | 6/1996 | Greenfield | |
| 5,554,166 A | 9/1996 | Lange et al. | |
| 5,575,403 A | 11/1996 | Charlton et al. | |
| 5,593,391 A * | 1/1997 | Stanners | 604/232 |
| 5,630,986 A | 2/1997 | Charlton et al. | |
| 5,624,458 A | 4/1997 | Lipscher | |
| 5,632,410 A | 5/1997 | Moulton et al. | |
| 5,636,640 A | 6/1997 | Staehlin | |
| 5,662,127 A | 9/1997 | De Vaughn | |
| 5,700,695 A | 12/1997 | Yassinzadeh et al. | |
| 5,714,390 A | 2/1998 | Hallowitz et al. | |
| 5,720,924 A | 2/1998 | Eikmeier et al. | |
| 5,738,244 A | 4/1998 | Charlton et al. | |
| 5,758,643 A | 6/1998 | Wong et al. | |
| 5,776,157 A | 7/1998 | Thorne et al. | |
| 5,779,677 A | 7/1998 | Frezza | |
| 5,788,651 A | 8/1998 | Weilandt | |
| 5,800,781 A | 9/1998 | Gavin et al. | |
| 5,801,057 A | 9/1998 | Smart et al. | |
| 5,810,199 A | 9/1998 | Charlton et al. | |
| 5,823,973 A | 10/1998 | Racchini et al. | |
| 5,829,589 A | 11/1998 | Nguyen et al. | |
| 5,830,219 A | 11/1998 | Bird et al. | |
| 5,846,490 A | 12/1998 | Yokota et al. | |
| 5,854,074 A | 12/1998 | Charlton et al. | |
| 5,855,501 A | 1/1999 | Lin et al. | |
| 5,863,800 A | 1/1999 | Eikmeier et al. | |
| 5,871,494 A | 2/1999 | Simons et al. | |
| 5,879,311 A | 3/1999 | Duchon et al. | |
| 5,880,829 A | 3/1999 | Kauhaniemi et al. | |
| 5,885,211 A | 3/1999 | Eppstein et al. | |
| 5,891,553 A | 4/1999 | Sesekura | |
| 5,916,229 A | 6/1999 | Evans | |
| 5,921,963 A | 7/1999 | Erez et al. | |
| 5,935,075 A | 8/1999 | Casscells et al. | |
| 5,938,679 A | 8/1999 | Freeman et al. | |
| 5,951,492 A | 9/1999 | Douglas et al. | |
| 5,951,582 A | 9/1999 | Thorne et al. | |
| 5,968,063 A | 10/1999 | Chu et al. | |
| 5,971,941 A | 10/1999 | Simons et al. | |
| 5,980,495 A * | 11/1999 | Heinz et al. | 604/263 |
| 5,989,227 A | 11/1999 | Vetter et al. | |
| 5,997,561 A | 12/1999 | Bocker et al. | |
| 6,014,577 A | 1/2000 | Henning et al. | |
| 6,022,324 A | 2/2000 | Skinner | |
| 6,027,459 A | 2/2000 | Shain et al. | |
| 6,032,059 A | 2/2000 | Henning et al. | |
| 6,036,924 A | 3/2000 | Simons et al. | |
| 6,048,352 A | 4/2000 | Douglas et al. | |
| 6,056,701 A | 5/2000 | Duchon et al. | |
| 6,071,294 A | 6/2000 | Simons et al. | |
| 6,090,078 A | 7/2000 | Erskine | |
| 6,093,156 A | 7/2000 | Cunningham et al. | |
| 6,099,484 A | 8/2000 | Douglas et al. | |
| 6,117,630 A | 9/2000 | Reber et al. | |
| 6,120,462 A | 9/2000 | Hibner et al. | |
| 6,132,449 A | 10/2000 | Lum et al. | |
| 6,136,013 A | 10/2000 | Marshall et al. | |
| 6,139,562 A | 10/2000 | Mauze et al. | |
| 6,143,164 A | 11/2000 | Heller et al. | |
| 6,152,942 A | 11/2000 | Brenneman et al. | |
| 6,155,992 A | 12/2000 | Henning et al. | |
| 6,156,051 A | 12/2000 | Schraga | |
| 6,159,424 A | 12/2000 | Kauhaniemi et al. | |
| 6,171,325 B1 | 1/2001 | Mauze et al. | |
| 6,176,865 B1 | 1/2001 | Mauze et al. | |
| 6,183,489 B1 | 2/2001 | Douglas et al. | |
| 6,193,673 B1 | 2/2001 | Viola et al. | |

(56) References Cited

U.S. PATENT DOCUMENTS

| | | |
|---|---|---|
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,245 B1 | 7/2001 | Kawai et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,358,265 B1 | 3/2002 | Thorne, Jr. et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,416,499 B2 * | 7/2002 | Paul, Jr. .................... 604/256 |
| 6,447,482 B1 | 9/2002 | Ronborg et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,537,257 B1 | 3/2003 | Wien |
| 6,616,616 B2 | 9/2003 | Fritz et al. |
| 7,396,334 B2 | 7/2008 | Kuhr et al. |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0082543 A1 | 6/2002 | Park et al. |
| 2002/0103499 A1 | 8/2002 | Perez et al. |
| 2003/0032681 A1 | 2/2003 | Coronado et al. |
| 2003/0083685 A1 | 5/2003 | Freeman et al. |
| 2003/0083686 A1 | 5/2003 | Freeman et al. |
| 2003/0088191 A1 | 5/2003 | Freeman et al. |
| 2003/0199896 A1 | 10/2003 | Boecker et al. |
| 2003/0199900 A1 | 10/2003 | Boecker et al. |
| 2003/0199901 A1 | 10/2003 | Boecker et al. |
| 2003/0199902 A1 | 10/2003 | Boecker et al. |
| 2003/0199904 A1 | 10/2003 | Boecker et al. |
| 2003/0199906 A1 | 10/2003 | Boecker et al. |
| 2003/0199908 A1 | 10/2003 | Boecker et al. |
| 2003/0199909 A1 | 10/2003 | Boecker et al. |
| 2003/0199910 A1 | 10/2003 | Boecker et al. |
| 2003/0199911 A1 | 10/2003 | Boecker et al. |
| 2003/0233112 A1 | 12/2003 | Alden et al. |
| 2003/0233113 A1 | 12/2003 | Alden et al. |
| 2004/0009100 A1 | 1/2004 | Simons et al. |
| 2004/0034318 A1 | 2/2004 | Fritz et al. |
| 2005/0021066 A1 | 1/2005 | Kuhr et al. |

FOREIGN PATENT DOCUMENTS

| | | |
|---|---|---|
| DE | 2 131 297 | 1/1973 |
| DE | 24 61 273 A1 | 9/1976 |
| DE | 28 03 345 | 6/1979 |
| DE | 38 42 317 | 6/1990 |
| DE | 9205278 U1 | 6/1992 |
| DE | 197 81 810 C2 | 5/1999 |
| DE | 100 47 419 A1 | 4/2002 |
| DE | 101 63 646 | 7/2003 |
| EP | 0 199 484 | 10/1986 |
| EP | 0 359 831 | 3/1990 |
| EP | 0 589 186 | 3/1994 |
| EP | 0 565 970 | 6/1994 |
| EP | 0 931 507 | 7/1999 |
| EP | 1 466 558 A2 | 8/2002 |
| GB | 1080986 | 8/1967 |
| GB | 2 331 936 A | 6/1999 |
| GB | 2 352 403 | 1/2001 |
| JP | 2-326247 | 7/1992 |
| JP | H04-194660 | 7/1992 |
| JP | 43 20 463 | 12/1994 |
| JP | H09-276235 | 10/1997 |
| JP | 10-296325 | 4/2000 |
| JP | 2000-116626 | 4/2000 |
| JP | 2000-116768 | 4/2000 |
| WO | 1993/02720 A1 | 2/1993 |
| WO | 1993/12726 A1 | 7/1993 |
| WO | 1996/02189 | 2/1996 |
| WO | 1997/42888 A1 | 11/1997 |
| WO | 1997/46157 A1 | 12/1997 |
| WO | 1998/14125 | 4/1998 |
| WO | 1998/48695 | 11/1998 |
| WO | 1999/29429 | 6/1999 |
| WO | 1999/26539 | 10/1999 |
| WO | 2000/40150 | 7/2000 |
| WO | 2001/00090 A1 | 1/2001 |
| WO | 2001/34029 A1 | 5/2001 |
| WO | 2001/66010 | 9/2001 |
| WO | 2002/056769 A1 | 7/2002 |
| WO | 2003/088834 | 10/2003 |

OTHER PUBLICATIONS

Elastizitat, CD Rompp Chemie Lexikon—Version 1.0 with Machine Translation, 1995.

Elastomere, CD Rompp Chemie Lexikon—Version 1.0 with Machine Translation, 1995.

TPE, CD Rompp Chemie Lexikon—Version 1.0 with Machine Translation, 1995.

Notice of Opposition to European Application No. 1 466 558 by Abbott Laboratories, Jun. 3, 2009.

Surelets Stick it to the Competition/Surelet Blood Lancets . . . In a Class by Themselves, Product Brochure, Gainor Medical, Long Beach, California.

Surelite . . . lancets that baby your skin, Packaging and Ordering Information, Gainor Medical, Long Beach, California.

* cited by examiner

BLOOD LANCET WITH HYGIENIC TIP PROTECTION

CROSS REFERENCE TO RELATED APPLICATIONS

This application is a continuation of U.S. patent application Ser. No. 10/204,568, filed Nov. 27, 2002 now abandoned, which was a National Stage of International Application No. PCT/EP01/02198, filed Feb. 28, 2001, which claims the benefit of German Patent Application No. 10010694.3, filed Mar. 4, 2000, which are hereby incorporated by reference in their entirety.

BACKGROUND

The invention concerns a lancet comprising a lancet needle with a tip and a lancet body which completely surrounds at least the tip region of the lancet needle. In addition the invention concerns a lancet comprising a lancet needle with a tip and a hollow body which surrounds at least the tip of the lancet needle. The invention also concerns a lancet magazine containing at least two lancets which each contain a lancet needle with a tip and which are each accommodated in individual chambers of the lancet magazine that are independent of one another, each chamber having at least one opening through which the tip of the lancet needle can emerge. Finally the invention concerns the use of an elastic material as a component of a lancet or lancet magazine.

The examination of blood samples in clinical diagnostics enables an early and reliable detection of pathological states and a specific and well-founded monitoring of physical conditions. Medical blood diagnostics always requires the collection of a blood sample from the individual to be examined. Whereas several milliliters of blood are often collected for the analysis of a person to be examined by venepuncture in hospitals and by physicians in private practice in order to carry out many laboratory tests, nowadays a few microliters of blood are usually sufficient for individual analyses of only one parameter. Such small amounts of blood do not require venepuncture. On the contrary, it is sufficient to obtain blood by pushing a sterile sharp lancet through the skin e.g. into the finger pad or earlobe of the person to be examined in order to collect a few microliters of blood for the analysis. This method is particularly suitable when it is possible to carry out the analysis of the blood sample immediately after blood collection.

Lancets and corresponding devices (so-called blood collection instruments, blood lancet devices or, as they are referred to in the following, lancing devices) which enable a substantially pain-free and reproducible blood collection are available especially in the so-called home-monitoring field i.e. where medical laymen themselves carry out simple analyses of the blood, especially for the regular blood withdrawal by diabetics which has to be carried out several times daily to monitor the blood glucose concentration. Furthermore the use of lancets with lancing devices is intended to lower the psychological barrier to piercing one's own body which is particularly important for children that suffer from diabetes and depend on regular blood glucose tests. Examples of lancets and lancing devices are the commercially available devices (lancing devices) and lancets: Glucolet® from the Bayer AG Company and Softclix® from Roche Diagnostics GmbH. Such lancets and devices (lancing devices) are for example the subject matter of WO-A 98/48695, EP-A 0 565970, U.S. Pat. No. 4,442,836 or U.S. Pat. No. 5,554,166.

The lancets of the prior art usually have a metal lancet needle with a tip which may be optionally sharpened. In many embodiments a plastic lancet body made of a rigid injection-mouldable material is injected onto the lancet needle to facilitate the handling of the lancet and optionally for its attachment in a lancing device. In the unused state the tip of the lancet needle is surrounded by a protective sheath to ensure its sterility. This sheath is usually composed of the same rigid material as the actual lancet body and then usually forms a single unit with this. The protective sheath can be separated from the lancet body and removed from the tip of the lancet needle before using the lancet. A predetermined breaking point is located between the lancet body and protective sheath for this purpose. After using the lancet, the tip of the lancet needle is unprotected and is thus a potential source of injury to the user and possibly other persons.

In order to avoid accidental injury on a used lancet needle, it is usually recommended that the users insert the tip of the lancet needle after use into the previously removed protective sheath. However, experience shows that not all users follow this advice and hence a large number of used lancets with unprotected tips are discarded. U.S. Pat. No. 5,304,192 and WO-A 96/02189 propose lancets as a solution to this problem in which the tip of the lancet needle can be pushed or pulled into the lancet body after use. Since in these cases the lancet body is manufactured from a non-elastic, substantially rigid or stiff material, the tip of the lancet needle, although it is concealed in the lancet body, is not completely hygienically protected because a channel remains in the material of the lancet body via which the lancet tip is in contact with the surroundings.

In the present commercially available systems the lancets are usually provided in a loose form for use in lancing devices. For each lancing process the user manually removes a lancet from a pack, for example a cardboard box or a tube containing a plurality of lancets which are usually in a disordered arrangement and loosely packed. Subsequently the lancing device is prepared for receiving the lancet by for example unscrewing or pulling off a protective cap to expose the lancet holder of the lancing device. The lancet holder is used to receive the lancets. It also guides the lancet during the actual lancing process. The lancet removed from the pack is manually inserted into the lancet holder of the lancing device and fixed there. Then the protective sheath that surrounds the lancet tip and protects the tip as well as the user has to be manually removed from the lancet. Subsequently the lancing device is sealed again with its protective cap. The protective cap ensures that the lancet is no longer accessible from outside. It usually has an opening through which the lancet tip can pass during the actual lancing process. Finally the lancing device is tensioned and is available for the lancing process to collect blood.

The many manual operating steps required for conventional lancet systems (lancet and lancing device) are felt to be disadvantageous by the user and are particularly problematic when perception is limited in a hypoglycaemic state. Moreover, the user is not prevented from using a once inserted lancet several times for lancing and collecting blood. This is risky for hygienic reasons especially when the lancet system is used by more than one person which for example may be the case in doctor's practices or hospitals. On the other hand, the repeated use of lancets also leads to increasing pain for the user since the lancets are designed for single use and rapidly become blunt when used several times. Furthermore with the lancing devices and lancets of the prior art there is a risk that lancing devices will be used with lancets that do not fit i.e. with lancets that are not suitable for a particular type of lancing device and thus lead to sub-optimal lancing results (reproducibility, lack of pain, amount of blood collected) or that the lancets are inserted incorrectly into the lancing devices. Furthermore a user can be accidentally injured when the lancets and lancing devices are used improperly.

There have therefore be no lack of attempts to eliminate the said disadvantages. Lancing devices are known from U.S. Pat. No. 5,514,152, U.S. Pat. No. 5,152,775, WO-A 98/14125, U.S. Pat. No. 3,030,959, U.S. Pat. No. 4,794,926 and U.S. Pat. No. 5,035,704 which store several lancets and can use these individually and in succession for lancing processes. After the lancing process the lancets can be removed individually from the device. However, these systems with lancet storage do not solve the above-mentioned problems of used lancets anymore than the systems which manually have to be individually loaded with lancets.

SUMMARY

In summary it can be ascertained that all designs of the prior art for lancets and lancet systems i.e. lancing devices or instruments in which lancets can be stored have the disadvantage that it is not possible to ensure the sterility, i.e. the asepsis, of the unused lancet needle and in particular its tip until immediately before the lancing process, and a safe and hygienic disposal of the once used lancet is completely left to the user. This is a considerable problem especially for systems in which unused lancets are stored together with used lancets i.e. in particular for lancet magazines and corresponding lancing devices which do not immediately eject a used lancet and instead store the used lancets until the entire store of lancets has been used up.

The object of the invention is to eliminate the disadvantages of the prior art. In particular the object of the present invention is to provide lancets in which at least the lancet needle tip is kept sterile, i.e. aseptic, in the unused state until immediately before use and can be stored hygienically in the used state. Ideally this object should be achieved without the user having to adopt separate measures for the hygienic storage. Moreover, the user should be protected from accidental injury by the lancet and in particular the used lancet.

The object is achieved by the subject matter of the invention as characterized in the patent claims.

The invention concerns a lancet containing a lancet needle with a tip and a lancet body which completely surrounds at least the tip region of the lancet needle, wherein the lancet body of the lancet according to the invention is composed of an elastic material at least in the tip region of the lancet needle in which the tip of the lancet needle is embedded.

The lancets according to the invention are designed for single use and should therefore also be referred to as single-use blood lancets or disposable blood lancets.

The lancet of the invention comprises a needle (lancet needle) with a tip. The needle is usually several millimeters (mm) to a few centimeters (cm) long and has an elongate shape. Needles typically have a cylindrical shape since this needle shape is particularly easy to manufacture; however, other needle shapes having different designs are also possible. The tip region of the needle comprises the needle tip which is inserted into the tissue when the lancet is used as directed. Hence the tip of the lancet needle is the part of the lancet which comes into contact with and may injure the skin of the individual to be pierced and thus causes a body fluid and in particular blood or interstitial liquid to flow out.

The tip of the lancet needle can for example be rotationally symmetrical as is generally the case for sewing needles. However, it has proven to be advantageous to provide the needle tip with one or several bevels. The edges formed in this manner which are slanted relative to the longitudinal axis of the needle and converge to form a tip, act as a sharp cutting edge in the piercing process and make the piercing process less painful than is the case with rotationally symmetrical needles.

The lancet needle of the lancet according to the invention is manufactured from a material which is hard enough to withstand mechanical stress without deformation during the piercing process, during the processing steps or other stresses which may occur. In addition the material must be such that no particles break off or become detached during the piercing process. Finally it must be possible to machine the needle in such a manner that the needle tip is sufficiently pointed and the edges of the needle tip can optionally be ground to a sufficient sharpness. Materials that are very suitable for the lancet needle are above all metals and of these especially high-grade steels. However, needles made of ceramics or plastics are also conceivable. High-grade steel needles are particularly preferred.

According to the invention at least the tip of the lancet needle of the lancet according to the invention is surrounded by a plastic body which is referred to as the lancet body in the following. An important feature is that the lancet body is composed of an elastic material in the tip region of the lancet needle. At least the tip of the lancet needle is completely surrounded on all sides by this elastic material i.e. it is embedded in it and thus sealed from the surroundings. The elastic material of the lancet body which in various embodiments can completely or only partially form the lancet body is characterized in that it is soft, deformable and can be pierced by the tip of the lancet needle without damaging the tip. In the lancing process, the lancet needle is moved along its longitudinal axis relative to the lancet body and its tip emerges from the lancet body in order to thus be able to pierce the skin of the individual to be examined in order to collect blood. Another important property is that the elastic material closes around the tip of the lancet needle when the lancet needle is optionally retracted into the lancet body. After the lancing process the lancet needle can be returned in a preferred embodiment to its initial position relative to the lancet body by reversing the piercing movement and in this position the tip is again completely enclosed on all sides by the elastic material of the lancet body.

The elastic material of the lancet body which completely encloses the tip of the lancet needle ensures the sterility of the lancet needle tip before use and preferably until immediately before use and optionally hygienically encloses the lancet needle tip after use. Consequently the elastic material is impenetrable to germs and prevents their entry or escape depending on whether the lancet needle is unused or used. In addition the elastic material represents a mechanical protection for the lancet needle tip and thus also prevents unintentional injury on the lancet needle tip.

Suitable elastic materials for the lancet body of the present invention have proven to be rubber, caoutchouc, silicone, elastomers and in particular thermoplastic elastomers. These have properties that are important for the present invention: they are soft, deformable, can be pierced by the lancet needle without damaging the tip and they form a tight seal around the used lancet needle tip. Furthermore they can be used for injection moulding processes which enables the lancets to be mass-produced in large numbers.

Thermoplastic elastomers which are also referred to as elastoplasts or thermoplasts or thermoplastic rubbers combine in the ideal case the handling properties of elastomers and the processing characteristics of thermoplasts. Thermoplastic elastomers are for example styrene-oligoblock copolymers (so-called TPE-S), thermoplastic polyolefins (TPE-O), thermoplastic polyurethanes (TPE-U), thermoplastic copolyesters (TPE-E) and thermoplastic copolyamides (TPE-A). Thermoplastic elastomers based on styrene-ethylene-butylene-styrene polymers (SEBS polymers, e.g. Evoprene® from Evode Plastics or Thermolast K from the Gummiwerk Kraiburg GmbH) have for example proven to be particularly suitable.

During the piercing process the lancet needle is moved relative to the lancet body. During this movement the latter is preferably fixed in its position by the lancing device or the lancing instrument. The lancet needle can have a special shape to enable it to be driven such as a needle head at the opposite end to the tip or it can have another lancet body in addition to the lancet body which surrounds the tip which is engaged by a drive element of the lancing device. The shape of the needle or of the additional lancet body can interact in a suitable manner with an appropriate drive device in the lancing instrument (lancing device).

In order to achieve the advantage that the lancet needle tip is hygienically enclosed by the elastic material of the lancet body before use and is also hygienically surrounded by the elastic material after use, it is of course necessary to return the lancet needle essentially to its original position relative to the lancet body containing the elastic material after use i.e. after the lancing process. This can be achieved by suitable interaction with a suitably adapted lancing device. In this connection it is only important that the lancet needle tip is again enclosed by the elastic material of the lancet body after use which thus prevents accidental injury on the needle tip.

In order to increase the stability of the elastic material, it is possible to combine it with a stiff material such as a stiff plastic material. In this case the outside of the elastic material which does not come into contact with the lancet needle can for example be stabilized with a layer of a stiff material such as a stiff plastic. It is also possible to manufacture only the lancet needle tip region of the lancet body from an elastic material and to manufacture the remaining lancet body from conventional stiff plastics. The elastic material and the stiff material can be glued together or joined together in an injection moulding process for example in a two-component injection moulding process. The stiff material of the lancet body mechanically stabilizes the elastic material during the lancing process and simplifies the fixing of the elastic part of the lancet body by the lancing device during the lancing process.

The invention additionally concerns a lancet containing a lancet needle comprising a tip and a hollow body which surrounds at least the tip of the lancet needle wherein the tip region of the lancet needle of the lancet according to the invention can move in the hollow body and the hollow body at least partially consists of an elastic material which can be pierced by the tip of the lancet needle during the lancing process and which optionally reseals the tip of the lancet needle in the hollow body when it is retracted.

Whereas in the case of the lancet described above according to a first aspect of the invention the tip region of the lancet needle is completely surrounded on all sides, and thus without any remaining hollow space around the tip, by an elastic material which embeds the lancet needle tip to ensure sterility before use and hygienic shielding after use, in a second aspect of the invention which is described now the tip of the lancet needle is surrounded by a hollow body which is closed on all sides. The regions of this hollow body which do not come into contact with the tip of the lancet needle are advantageously manufactured from a stiff and preferably injection mouldable material. An essential feature of the invention is that the region of the hollow body which is pierced by the lancet needle tip during the lancing process consists of an elastic material.

During the lancing process the lancet needle is moved relative to the hollow body which represents the lancet body. The holder and drive for the lancet needle and the attachment of the lancet body can be realised as described above by suitable constructional measures.

The elastic material which comprises a part of the hollow lancet body is pierced by the lancet needle tip during the lancing process and optionally reseals after the lancet needle tip has been retracted again into the hollow body and thus seals the hollow body. Hence the lancet needle tip is sealed in a sterile manner in the hollow body until immediately before use and is hygienically enclosed in it after use.

The lancet of this embodiment can, like the lancet of the alternative embodiment described above, in addition to the lancet body which encloses the tip of the lancet needle, have a further lancet body which interacts with suitable elements of a lancing device during the lancing process. In addition the lancet needle can have a special shape, for example it can have a head at the end opposite to the tip.

With regard to the properties of the elastic material and the connection of the elastic material with the stiff material of the lancet body, the same applies as already stated above for the first embodiment of the invention.

An additional subject matter of the invention is a set of lancets which contains at least two of the lancets according to the invention that are connected together. This is the third subject matter of the invention.

The lancets of the set of lancets according to the present invention can be of such a type that the lancet needle tip is completely surrounded or embedded on all sides by an elastic material without any remaining hollow space around the tip, or of a type where the lancet needle tip is enclosed in a hollow body. The individual lancets, which in turn are each composed of at least a lancet needle and a lancet body, are connected together in the set of lancets according to the invention. The connection is advantageously via the lancet body. Identical lancets are preferably connected together.

The lancets in the set of lancets can either be connected by thin bars or cross-pieces or be attached to a carrier tape made for example of paper or plastic. The lancets are preferably connected in such a manner that the individual lancet needles of the individual lancets of the set of lancets are enclosed in a continuous piece of the elastic material. In this case the elastic material can be in the form of an elastic tape. The elastic tape as a connecting means for several and preferably several identical lancets is particularly suitable for lancets of the first subject matter of the invention i.e. lancets in which the lancet needle tip is completely embedded in the elastic material. However, an elastic tape material can also be used as a connecting material for lancets of the second subject matter of the invention i.e. lancets which have a hollow body around the lancet needle tip.

Another subject matter of the invention is a lancet magazine with chambers for storing lancets. The magazine according to the invention contains at least two lancets which each contain a lancet needle with a tip and which are each accommodated in individual chambers of the lancet magazine which are independent of one another. Each chamber has at least one opening through which the tip of the lancet needle emerges. The lancet magazine of the present invention is characterized in that the said opening of the chamber is sealed by an elastic material. The elastic material is pierced by the tip of the lancet needle during the lancing process and optionally reseals after the tip of the lancet needle has been retracted again into the chamber.

Like the set of lancets according to the third subject matter of the invention, the lancet magazine (fourth subject matter of the invention) is used for the common storage of unused lancets (cassetting) and optionally also to store used lancets (recassetting). In contrast to the set of lancets, the individual lancets in the lancet magazine are not directly joined together but are located in individual chambers of the magazine. Here they are independent of one another. The chambers in the magazine are disposed in an essentially regular geometric pattern where neighbouring chambers have at least one and preferably two common wall(s).

The individual chambers of the magazine have at least one opening for the tip of the lancet needle. According to the invention this opening is closed by an elastic material which has the properties mentioned above in connection with the first subject matter of the invention. The tip of the lancet needle can penetrate through the elastic material during the lancing process. The elastic material optionally reseals when the lancet needle tip is retracted into the chamber of the lancet magazine. The chamber is then again tightly sealed.

The chambers of the lancet magazine can be sealed by suitable constructional measures in such a manner that the tip region of the lancet needle is sterile before use and is optionally hygienically shielded from the environment after use. For example the lancet can have a lancet body which, by means of suitable forming, interacts with the inner wall of the chamber of the lancet magazine to form a seal. It is important for the invention only that the opening of the chamber through which the lancet needle tip passes during the lancing process is closed by the elastic material.

The individual chambers can be arranged in any manner in the lancet magazine. For example a plurality of lancet chambers can be arranged next to one another resulting in an essentially cuboid or bar-shaped magazine. The chambers may also be arranged symmetrically around a central axis resulting in a lancet magazine in the shape of a cylinder (like the cylinder of a revolver). However, other arrangements are also conceivable and feasible.

Finally the invention concerns the use of an elastic material as a component of a lancet or a lancet magazine where the elastic material is used to maintain the sterility of at least the tip of a lancet needle in the unused state. In a preferred embodiment the elastic material can also be used to hygienically shield at least the tip of a lancet in the used state.

The use of an elastic material according to the invention to protect the tip of the lancet needle ensures the sterility of an unused lancet needle tip and optionally hygienically screens the used lancet needle tip.

The lancet needle tip can be sterilized in the unused state by suitable measures such as gamma irradiation. Once sterilized the lancet needle tips remains sterilized by means of the appropriate lancet body or an appropriate lancet magazine which inter alia consist of an elastic material. In contrast to the prior art where up to now no elastic materials have been described for shielding the lancet needle tips, the use of the elastic material according to the present invention also allows a hygienic sheathing of the used lancet needle tip. A channel which may be present for a short time through which the lancet needle can pass for the purpose of piercing is sealed again by the elastic material after the lancet needle is retracted i.e. after the lancing process is completed. Hence contaminants adhering to the lancet needle tip after the lancing process and in particular germs and infectious material cannot reach the surroundings. This is particularly advantageous for disposable lancets which are individually disposed off after use. However, this property is extremely important for sets of lancets and lancet magazines in which used lancets are also stored next to unused lancets which can then be disposed off as a whole.

The invention has the following advantages:

In all embodiments the tip of the lancet needle is shielded in a germ-tight manner in the unused state i.e. germs cannot penetrate through to the lancet needle tip until immediately before the lancet is used. After suitable sterilization the lancet tips remain sterile for a long period.

In all embodiments the tip of the lancet needle can be hygienically protected in the used state. An accidental contamination of the environment (user, objects, other lancets) is substantially prevented.

The user of the lancets according to the invention is protected from accidental injury on a used lancet needle. The same also applies to persons other than the actual user.

The lancets and sets of lancets according to the invention can be manufactured cost-effectively in large numbers with conventional injection moulding processes.

The lancets and sets of lancets according to the invention can be considerably miniaturized and are therefore suitable for use in compact, automated systems.

BRIEF DESCRIPTION OF THE DRAWINGS

The invention is further elucidated by the following FIGS. 1 to 6.

The numbers in the figures denote:
1 lancet needle
2 tip of the lancet needle
3 lancet body made of elastic material
3' edge of the lancet body 3
4 stabilizing layer
5 lancet body made of rigid material
5' projecting part of the lancet body
6 seal made of elastic material
7 lancet body
8 chamber wall
9 lancet body
10 lancet
11 set of lancets
12 lancet (10) in chamber

DESCRIPTION OF THE SELECTED EMBODIMENTS

Figure 1:
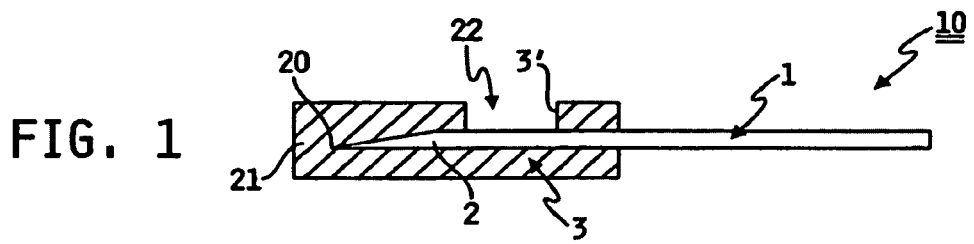
FIG. 1 shows a schematic longitudinal section through a preferred embodiment of a lancet according to the invention.
Figure 1A:
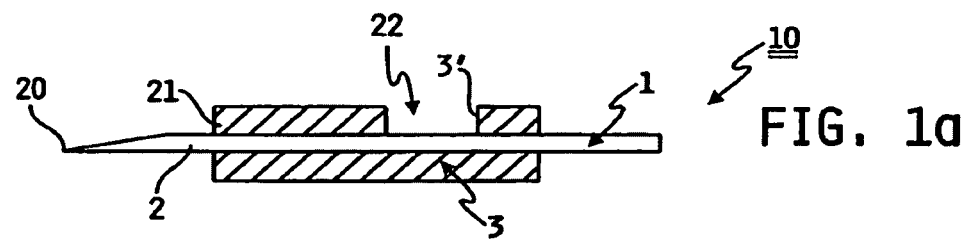
Figure 7:
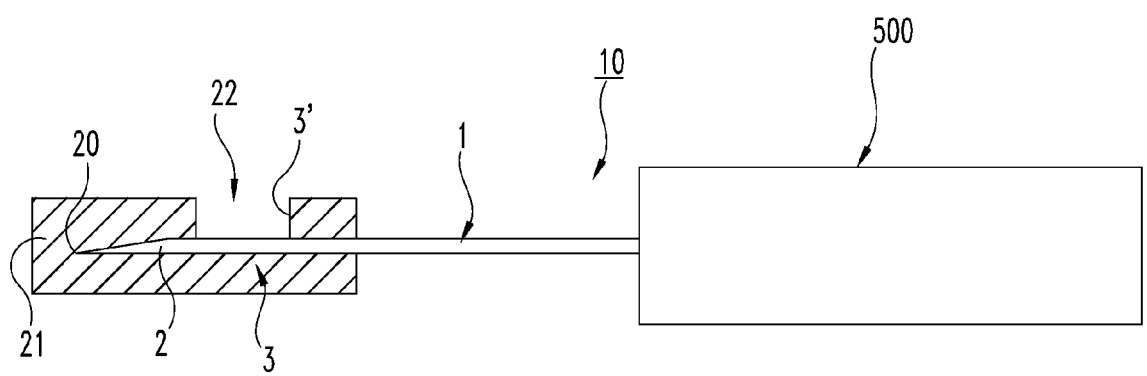
FIG. 7 shows a schematic longitudinal section through the FIG. 1 lancet engaging a lancing device.

The preferred embodiment of the lancet (10) according to the invention shown in FIG. 1 contains a lancet needle (1) the tip region (2) of which is surrounded by a lancet body (3) which is manufactured from an elastic material. The tip (2) of the lancet needle (1) is completely surrounded by the elastic material of the lancet body (3). Outside the region of the tip (2) of the lancet needle (1), the lancet body (3) has a recess such that the lancet body (3) has an edge (3') at least on one side that can interact with appropriate gripping or holding devices in a lancing device in order to hold the lancet body (3). It is necessary to hold the lancet body (3) because the lancet needle (1) has to be moved relative to the lancet body (3) during the lancing process and must be able to pass through it in the tip region (2) of the lancet needle (1). FIG. 1a shows the lancet (10) at the end of the forwards movement of the lancing process. FIG. 7 shows one example of the lancet (10) coupled to a lancing device (500).

The recess in the lancet body (3) also serves to reduce the frictional forces between the lancet needle (1) and lancet body (3) during the lancing movement.

The cross-section of the lancet needle (1) and of the lancet body (3) perpendicular to the longitudinal axis of the needle preferably has a round shape. However, the cross-section can also have any other shape, for example quadratic or rectangular. It is also not necessary for the lancet needle (1) and the lancet body (3) to have the same cross-sectional shape. For example the lancet needle (1) can have an essentially round cross-section and the lancet body (3) can have a rectangular cross-section.

Figure 2:
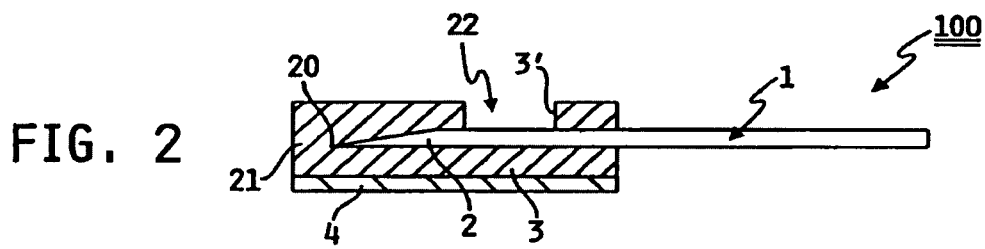
FIG. 2 shows a schematic longitudinal section through an alternative, equally preferred embodiment of a lancet according to the invention.

FIG. 2 shows a schematic longitudinal section of another equally preferred embodiment of a lancet (10) according to the invention. The lancet (10) is composed of essentially the same elements as the lancet (10) shown in FIG. 1. In contrast to the lancet (10) shown in FIG. 1, a stabilizing layer (4) is applied to one side of the lancet body (3) which is composed of an elastic material. This stabilizing layer (4) can be glued onto the lancet body (3). However, it is preferred that the stabilizing layer (4) is joined together with the lancet body (3) in an injection moulding process with the lancet needle (1).

The purpose of the stabilizing layer (4) is to prevent deformation of the elastic lancet body (3) during the lancing process. In particular it should prevent stretching of the lancet body (3).

Figure 3:
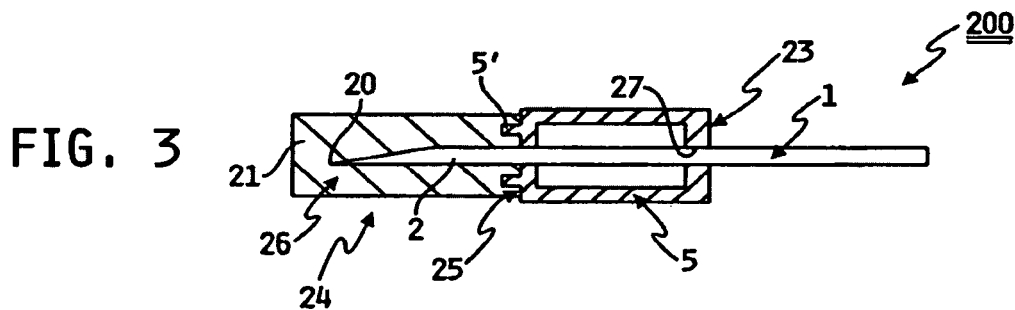
FIG. 3 shows a schematic longitudinal section through another alternative of a preferred embodiment of the lancet according to the invention.

Another preferred embodiment of the lancet (10) according to the invention is shown in FIG. 3 in a schematic longitudinal section. The lancet body (3, 5) of the lancet (10) consists in this case of two different components. The tip (2) of the lancet needle (1) is enclosed by a lancet body (3) made of an elastic material. The lancet needle (1) is joined to a lancet body (5) made of a rigid material at a distance from the tip region (2) of the lancet needle (1). The lancet body (5) made of rigid material is in turn joined to the lancet body (3) made of elastic material. In order to enlarge the joining surface between the elastic lancet body material (3) and the rigid lancet body material (5), the rigid lancet body material (5) can have projecting parts (5'). The rigid and elastic material (3, 5) of the lancet body can in turn be joined by gluing or two-component injection moulding.

Whereas in the case of the embodiments of FIGS. 1 and 2, the lancet body (3) is held during the lancing process by direct action on the elastic material of the lancet body (3), in the embodiment of FIG. 3 the lancet body (5), which consists of a rigid material, is held during the lancing process. In this case the lancet needle (1) is moved along its longitudinal axis. During this process it penetrates the surface of the elastic lancet body (3). After the lancing process, the lancet needle (1) is retracted such that the elastic lancet body (3) can again be positioned around the tip (2) of the lancet needle (1). The lancet body (3, 5) is fixed in its position during the lancing process.

Figure 4:
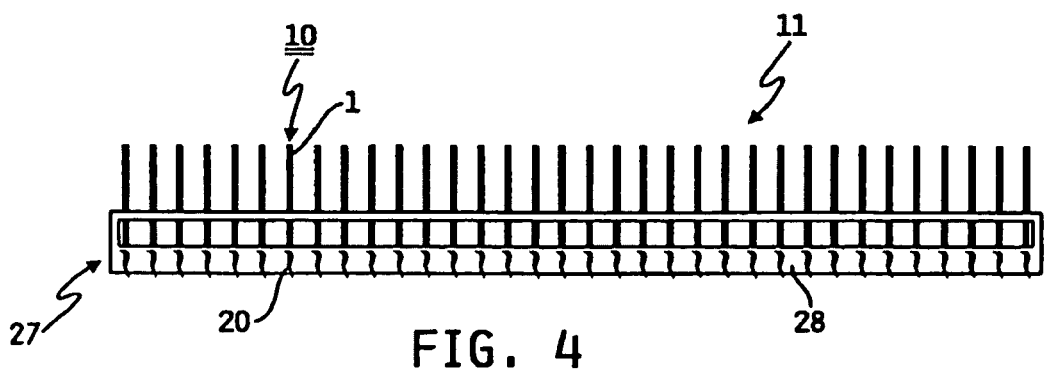
FIG. 4 shows a schematic top-view of a preferred embodiment of a set of lancets according to the invention.

FIG. 4 shows a schematic top-view of a set of lancets (11). A plurality of lancet needles (1) with a tip (2) are embedded in this embodiment of the set of lancets (11) in a single tape-like lancet body (3) made of elastic material. The set of lancets (11) is suitable for use in an automated system in which a plurality of lancets is stored and can be used individually for lancing processes.

A longitudinal section through the longitudinal axis of an individual lancet of a set of lancets (11) would correspond essentially to the lancet (10) shown in FIG. 1 or 2. The set of lancets (11) can, like the lancet of FIG. 2, have a stabilizing layer (4) (not shown in FIG. 4). This stabilizes the set of lancets (11) as a whole and the individual lancets contained therein not only during the lancing process but also strengthens them mechanically which can for example be advantageous for the automated handling of the set of lancets (11) in a mechanical system for storing and using lancets.

Since the lancet body (3) of the set of lancets (11) consists of an elastic material, it is possible to compactly package the entire set of lancets (11) for example by rolling them together spirally around the longitudinal axis of the first lancet needle (2) in the set of lancets (11).

Figure 5:
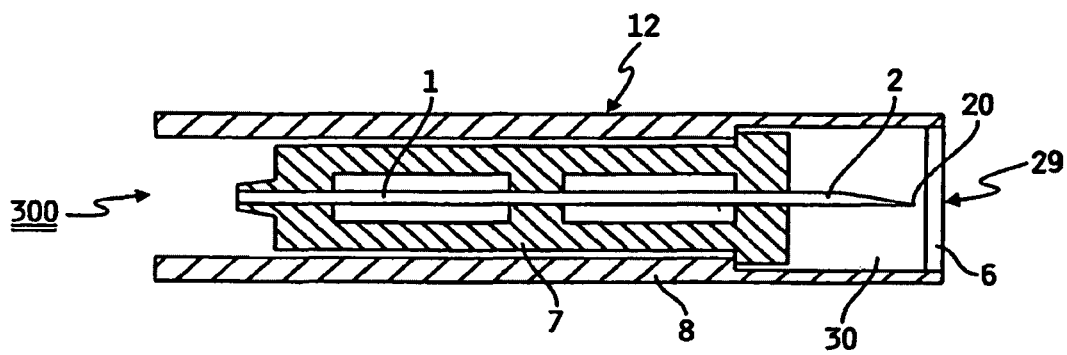
FIG. 5 shows a schematic longitudinal section through a chamber of a preferred lancet magazine according to the invention including a lancet located therein.

FIG. 5 shows a schematic longitudinal section through a chamber of a lancet magazine which contains a lancet (10). The individual chambers can be arranged in any desired manner in the lancet magazine. For example the chambers can be arranged next to or behind one another and thus form an essentially cuboid shaped magazine or be radially arranged around a central axis and thus form an essentially cylindrical or barrel-shaped magazine. The lancet (10) is enclosed in the chamber by the chamber walls (8). In the embodiment shown in FIG. 5 the lancet body (7) which surrounds the lancet needle (1) and the chamber wall (8) have a matching complementary shape such that the tip region (2) of the lancet needle (1) is in a closed hollow space. In addition to the chamber wall (8) and the lancet body, the hollow space is also closed by a seal (6) made of elastic material. The seal (6) can be pierced during the lancing process by the tip (2) of the lancet (10) and reseals after the lancet (10) is retracted into the chamber of the magazine like the septum of a glass ampoule which is for example used to store vaccines. The seal (6) made of elastic material thus ensures a hygienic storage and disposal of an already used lancet (10).

Figure 6:
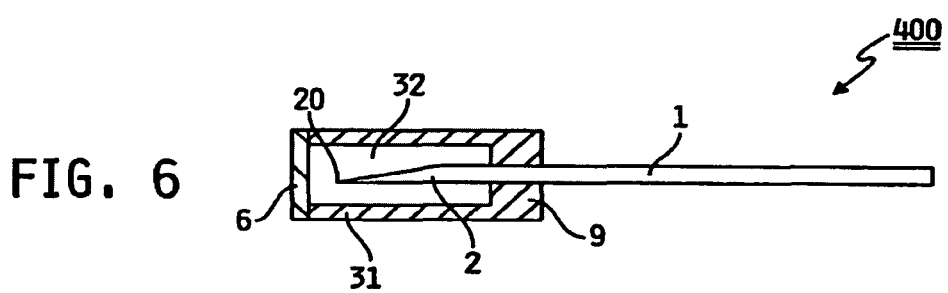
FIG. 6 shows a further preferred embodiment of a lancet according to the invention in a schematic sectional view.
Figure 6A:
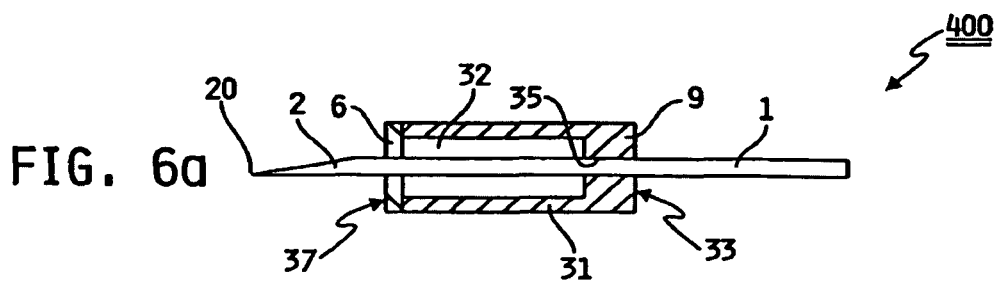

The seal (6) of the lancet body (9) in the lancet (10) of FIG. 6 has a similar septum function. This lancet (10) consists of a lancet needle (1) with a tip (2) which is located in a closed hollow space which is formed by the lancet body (9) which is manufactured from a rigid material and the seal (6) made of elastic material. During the lancing process the lancet needle (1) glides along its longitudinal axis with its tip (2) facing forwards whereas the lancet body (9) is held stationary by suitable means in a lancing device. In this process the tip (2) of the lancet needle (1) pierces the seal (6) made of elastic material. FIG. 6a shows the lancet (10) at the end of the forwards movement of the lancing process.

The elastic material properties of the seal (6) ensure that the hollow space is resealed after retracting the lancet needle (1) after the lancing process and in particular after retracting the tip (2) of the lancet needle (1) into the hollow space of the lancet body (9).

What is claimed is:

1. Lancet containing
a lancet needle with a tip;
a lancet body which completely surrounds the lancet needle at least in the area of the tip, the tip being able to move relative to the lancet body and able to protrude from the lancet body and the lancet body consisting of an elastic material at least in the area of the tip of the lancet needle, characterized in that before its use, the tip of the lancet needle is embedded in the elastic material without a hollow space remaining, wherein the elastic material is a thermoplastic elastomer;
wherein the tip of the lancet needle has a first position in which the tip is embedded within the elastic material of the lancet body;
wherein the tip of the lancet needle has a second position in which the tip protrudes from the lancet body;
the tip of the lancet needle being moveable from the first position to the second position;
and a lancing device having a drive device engaging the lancet needle to move the tip of the lancet needle from the first position to the second position.

2. Lancet according to claim 1, characterized in that the elastic material is stabilized with a stiff material.

3. Lancet set comprising at least two lancets according to claim 1 which are connected together.

4. Lancet set according to claim 3, characterized in that the lancets are connected together by the elastic material.

5. Lancet according to claim 1, wherein the lancet needle is directly attached to the drive device.

6. Lancet according to claim 1, wherein the tip of the lancet needle pierces the elastic material and tissue when moving from the first position to the second position.

7. Lancet according to claim 1, further comprising:
the lancet body having a tissue facing surface configured to face tissue during lancing and a lancing device facing surface facing the lancing device;
wherein the tip of the lancet is located between the tissue facing surface and the lancing device facing surface when in the first position; and
wherein the tip of the lancet extends from the tissue facing surface when in the second position.

8. Lancet according to claim 7, further comprising:
the lancet needle having a drive end opposite the tip where the lancing device actuates the lancet needle; and
wherein a length of the lancet needle from the lancet body to the drive end is bare to allow the lancet needle to move relative to the lancet body when the tip of the lancet needle moves from the first position to the second position.

9. Lancet according to claim 8, wherein the drive end of the lancet needle is solely attached to the lancet body through the lancet needle.

10. Lancet according to claim 1, wherein the thermoplastic elastomer is based on styrene-ethylene-butylene-styrene polymers.

11. Lancet, comprising:
a lancet needle with a tip; and
a lancet body which completely surrounds the lancet needle at least in the area of the tip, the tip being able to move relative to the lancet body and able to protrude from the lancet body and the lancet body including an elastic material at least in the area of the tip of the lancet needle, characterized in that before its use, the tip of the lancet needle is embedded in the elastic material without a hollow space remaining, wherein the elastic material is an injection moldable material.

12. Lancet according to claim 11, further comprising:
the lancet needle having a drive end opposite the tip; and
wherein a length of the lancet needle from a lancet body to the drive end is bare to allow the lancet needle to move relative to the lancet body.

13. Lancet according to claim 12, wherein the drive end of the lancet needle is solely attached to the lancet body through the lancet needle.

14. Lancet according to claim 12, wherein the drive end of the lancet needle is dull.

15. Lancet according to claim 14, wherein the drive end of the lancet needle includes a head.

16. Lancet according to claim 11, wherein the injection moldable material includes a thermoplastic elastomer.

* * * * *